US012622987B2

(12) United States Patent
Doshi

(10) Patent No.: US 12,622,987 B2
(45) Date of Patent: May 12, 2026

(54) AUTOMATED DEVICE FOR DISINFECTION OF STETHOSCOPE HEAD PIECE USING DUAL MEANS SIMULTANEOUSLY

(71) Applicant: Arpan Rameshchandra Doshi, Sugar Land, TX (US)

(72) Inventor: Arpan Rameshchandra Doshi, Sugar Land, TX (US)

(73) Assignee: Arpan Rameshchandra Doshi, Sugar Land, TX (US)

( * ) Notice: Subject to any disclaimer, the term of this patent is extended or adjusted under 35 U.S.C. 154(b) by 859 days.

(21) Appl. No.: 18/052,911

(22) Filed: Nov. 5, 2022

(65) Prior Publication Data

US 2024/0148922 A1      May 9, 2024

(51) Int. Cl.
| | |
|---|---|
| *A61L 2/00* | (2006.01) |
| *A61L 2/10* | (2006.01) |
| *A61L 2/24* | (2006.01) |
| *B08B 3/00* | (2006.01) |
| *B08B 7/04* | (2006.01) |
| *B08B 9/00* | (2006.01) |

(52) U.S. Cl.
CPC .. *A61L 2/10* (2013.01); *A61L 2/24* (2013.01)

(58) Field of Classification Search
CPC ..... A61L 2/00; A61L 2/10; A61L 2/24; A61L 2/16; A61L 2/18; A61L 2202/17; A61L 2202/24; A61L 2202/11; B08B 9/02; B08B 13/00; B08B 3/02

USPC ......... 422/1, 28, 62, 292, 295, 300; 134/18, 134/22.12, 36, 60, 137, 201
See application file for complete search history.

(56) References Cited

U.S. PATENT DOCUMENTS

| | | | | |
|---|---|---|---|---|
| 7,850,905 | B2 * | 12/2010 | Petersen | A61L 2/18 422/27 |
| 8,506,726 | B2 * | 8/2013 | Cui | A61B 90/70 134/57 R |
| 2005/0196314 | A1 * | 9/2005 | Petersen | A61B 90/70 422/62 |
| 2009/0044845 | A1 * | 2/2009 | Cui | A61B 1/123 134/201 |
| 2013/0098407 | A1 * | 4/2013 | Perlman | A61B 90/70 49/260 |

* cited by examiner

*Primary Examiner* — Monzer R Chorbaji

(57) ABSTRACT

The embodiments herein relate to a device for disinfection of stethoscope headpiece using dual means working simultaneously. The device of the present invention provides a two-advantage system of simultaneously using photo and chemical disinfection methods. According to an embodiment herein, the device comprises a disinfection chamber equipped with photo-disinfection means having multiple ultraviolet-C LED radiation lamps and chemical disinfection means having chemical spray nozzles. The device of the present invention has an additional functionality of disinfecting stethoscope headpiece using chemical liquid spray making the disinfection process more efficient and a reduced disinfection time.

20 Claims, 7 Drawing Sheets

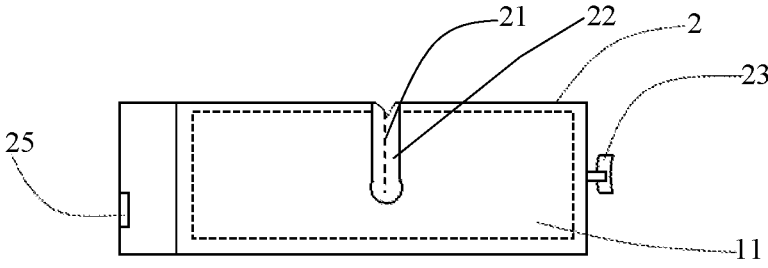
FIG. 5
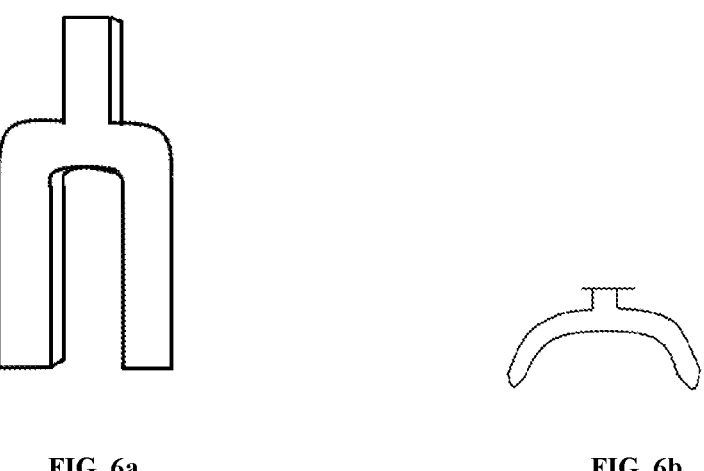
FIG. 6a
FIG. 6b

21

21

AUTOMATED DEVICE FOR DISINFECTION OF STETHOSCOPE HEAD PIECE USING DUAL MEANS SIMULTANEOUSLY

BACKGROUND

Technical Field of Invention

The embodiments herein generally relate to medical equipments and particularly to a medical equipment disinfection device. The embodiments herein more particularly relate to an automated device for disinfection of stethoscope head piece using UV-C and chemical method simultaneously.

Description of Related Art

Healthcare Associated Infections (HAI) are a significant public health problem worldwide with significant negative consequences, including impairment of patients' health, mortality, longer hospitalization with the need for longer treatment and associated higher costs. It has been seen that more than 32% of HAI are avoidable through proper hand washing and disinfection of medical devices between patients. The hands of healthcare professionals are said to be the main vehicle for the transmission of microbes, but also the medical devices (such as stethoscopes, otoscopes, and thermometers) are considered a source of transmission of microorganisms to patients.

A variety of factors have been determined to contribute to the distribution of nosocomial infections. Nosocomial infections often result from inadequate or superficial management of cleaning, disinfection, and sterilization. All objects that come into contact with and are shared between personnel and patients are possible carriers of microorganisms. The handheld medical devices such as stethoscopes are of main concern. Unfortunately, although these instruments are in direct contact with many patients every day, their proper disinfection is not an established practice.

Stethoscopes are the most customary medical equipment wield by physicians daily. The function of the stethoscope is to detect sounds coming from the patient's organs so that they can be interpreted to determine physiological or pathological conditions. There is a direct contact between its head with the various parts of the patient. It has been conclusively demonstrated that their membranes can transmit microbes and viruses from one patient to another and from health care worker to patient. Stethoscopes, if not disinfected, can cause cross-contamination. With the rise of potential infections in the healthcare setups, disinfection of this medical equipment is very much important.

The simplest solution to the problem is to disinfect the stethoscope membrane before each use, to avoid contamination and its build-up with repeated uses. Unfortunately, this is rarely done in clinical practice, for various reasons, including poor hygiene practices by medical staff, forgetfulness in managing the various stages of medical care, lack of awareness/consideration of the importance of the procedure, and the cumbersome process of disinfecting with swabs moistened with chemical disinfectant.

Where medical staff repeatedly pass from one patient to another, for example, when a doctor is making hospital rounds or nursing staff are routinely tending patients, the manual effort required to clean a stethoscope for each patient would significantly detract from the time available to examine each patient. The result is that reuse of a stethoscope without sufficient cleaning care being undertaken can result in the transfer of infectious or other organisms between patients.

Traditional practice for cleaning and disinfecting stethoscope includes use of a cleansing agent such as an alcohol swab to wipe diaphragms or use disinfectants such as chlorhexidine, isopropyl alcohol, triclosan to inhibit decontamination of stethoscope. However, studies have shown that such traditional cleaning or disinfection procedures are often inadequate to completely destroy contaminants if indeed, they are carried out.

Hence, the disinfection of stethoscope is a big challenge. One reason for this is that the currently available stethoscope designs are very sensitive to autoclave, thermal, gas, and chemical sterilization methods which can damage the diaphragm or other sensitive parts of the stethoscope.

There have been prior arts which disclose use of UV-C light alone for disinfecting stethoscope. Miniaturization of UV-LED technology, as well as its low power consumption, long life, and decreasing cost, allow innovative applications for disinfection in the biomedical field.

In view of foregoing, there is a need to develop a simple and portable device for disinfecting the stethoscope head piece while the doctor is working with several patients. There is also a need to develop a device for disinfecting stethoscope head piece that has dual working mechanism of UV-C disinfection and chemical disinfection simultaneously.

The value additions and above-mentioned shortcomings, disadvantages and problems are addressed herein, as detailed below.

SUMMARY OF THE INVENTION

Thus, the primary object of the embodiments herein is to provide an automated device for disinfection of medical-healthcare instruments, especially the head piece of a stethoscope.

Another object of the embodiments herein is to provide an automated device for disinfection of stethoscope head piece in a sufficiently short period of time so that the disinfection procedure does not interfere with a health care provider's ability to examine patients in a timely manner.

Yet another object of the embodiments herein is to provide an automated device for disinfection of stethoscope headpiece having a dual working mechanism for cleaning the stethoscope device in an efficient manner, wherein the dual mechanism comprises UV-C radiation and chemical disinfection method.

Yet another object of the embodiments herein is to provide an automated device for disinfection of stethoscope wherein the device is compact in size and weight making it truly a portable device.

Yet another object of the embodiments herein is to provide an automated device for disinfection of stethoscope having an ease of operation while loading or unloading the stethoscope or its head piece.

Yet another object of the embodiments herein is to provide an automated device for disinfection of stethoscope providing a reduced disinfection cycle time allowing the operator to repeat after each use in a short time.

Yet another object of the embodiments herein is to provide an automated device for disinfection of stethoscope that is simple, efficient and economical to make.

These and other objects and advantages of the embodiments herein will become readily apparent from the following detailed description taken in conjunction with the accompanying drawings.

According to an embodiment herein, an automated device 100 for disinfection of stethoscope headpiece using dual means working simultaneously is provided. The device 100 comprises a housing 2, at least two chamber present inside the housing 2, wherein one chamber is a disinfection chamber 10 and another chamber is a chemical holding chamber 11. The device 100 further comprises a plurality of spray tubes 15 and nozzles 18, a plurality of UV-C light source 14 present inside the disinfection chamber 10, a holder 13 present inside the disinfection chamber 10, at least two doors 4 hinged with the chambers 10 and 11, respectively, an air vent 20 present in the disinfection chamber 10, a bottom outlet 21 sealed with a rubber gasket 22 present at the bottom of the housing passing through the disinfection chamber 10 and a power supply.

According to an embodiment herein, the plurality of spray tubes 15 and nozzles 18 are present in the disinfection chamber 10.

According to an embodiment herein, the chemical holding chamber 11 is present on top side of the disinfection chamber 10.

According to an embodiment herein, the chemical holding chamber 11 holds a bag 16 of a chemical. The chemical is alcohol according to an embodiment herein. The chemical is isopropyl alcohol, according to another embodiment herein.

According to an embodiment herein, the holding chamber 11 has a slight slope 24 with top part of the chamber at higher elevation than the bottom part of the chamber.

According to an embodiment herein, the plurality of spray tubes 15 deliver the chemical from the bag 16 kept inside the chemical holding chamber 11 to the disinfection chamber 10 through spray tubes 15 and nozzles 18.

According to an embodiment herein, the chemical moves out from an opening 17 present in the bag 16 to the spray tubes 15.

According to an embodiment herein, the holder 13 is a U-shaped holder which is detachable to hold a stethoscope head piece, and wherein the holder 13 is positioned at the centre of the disinfection chamber 10.

According to an embodiment herein, the nozzles 18 are communicated to the holding chamber 11 through a plurality of tubes 15.

According to an embodiment herein, the disinfection chamber 10 is equipped with the ultraviolet-C ray disinfection lamps, wherein at least one ultraviolet-C ray disinfection lamps is located on each side of the chamber 10. According to another embodiment herein, at least one ultraviolet-C ray disinfection lamp is located on a top side, at least one is located on a right side and at least one is located on a left side of the disinfection chamber 10.

According to an embodiment herein, the spray nozzles (18a, 18b) are located on a left side and a right side inner wall of the disinfection chamber 10.

According to an embodiment herein, the spray nozzles (18a, 18b) spray the chemical from the bag 16 on the stethoscope headpiece placed on the holder 13 inside the disinfection chamber 10 when a power button is 'ON'.

According to an embodiment herein, the bottom outlet 21 sealed with a rubber gasket 22 allows passage of the stethoscope tube.

According to an embodiment herein, the air vent 20 is located on at least one side of the disinfection chamber 10.

According to an embodiment herein, the chemical bag is disposable and is replaced when the chemical gets over by opening the door.

According to an embodiment herein, a control panel 12 is present on the housing 2, wherein the control panel 12 comprises a plurality of control keys, a timer display, indicator lights, a controller, and a power supply unit.

According to an embodiment herein, an external holder 23 is present on an outer side of the housing 2 for holding the earpiece of the stethoscope.

According to an embodiment herein, the controller is equipped with a programmable microchip or microcontroller.

According to an embodiment herein, the stethoscope head piece disinfection device can be used in both vertical and horizontal orientation.

According to an embodiment herein, the device takes less than 3 minutes for simultaneous disinfection of stethoscope headpiece.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF DRAWINGS

The other objects, features and advantages will occur to those skilled in the art from the following description of the preferred embodiment and the accompanying drawings in which:

FIG. 5 is a bottom side schematic view of the automated device 100 for disinfection of stethoscope headpiece using dual means working simultaneously, according to an embodiment herein.

FIG. 6a is a top view of the stethoscope head holder 13 and FIG. 6b is a top view of the external earpiece holder 23, according to an embodiment herein.

FIG. 7a to FIG. 7d shows the shape of the chemical bag 16, wherein FIG. 7a is a front view of the chemical bag, wherein FIG. 7b is a right-side view of the chemical bag, wherein FIG. 7c is a left side view of the chemical bag and wherein FIG. 7*d* is a back view of the chemical bag, according to embodiments herein.

DETAILED DESCRIPTION OF EMBODIMENTS

Figure 1:
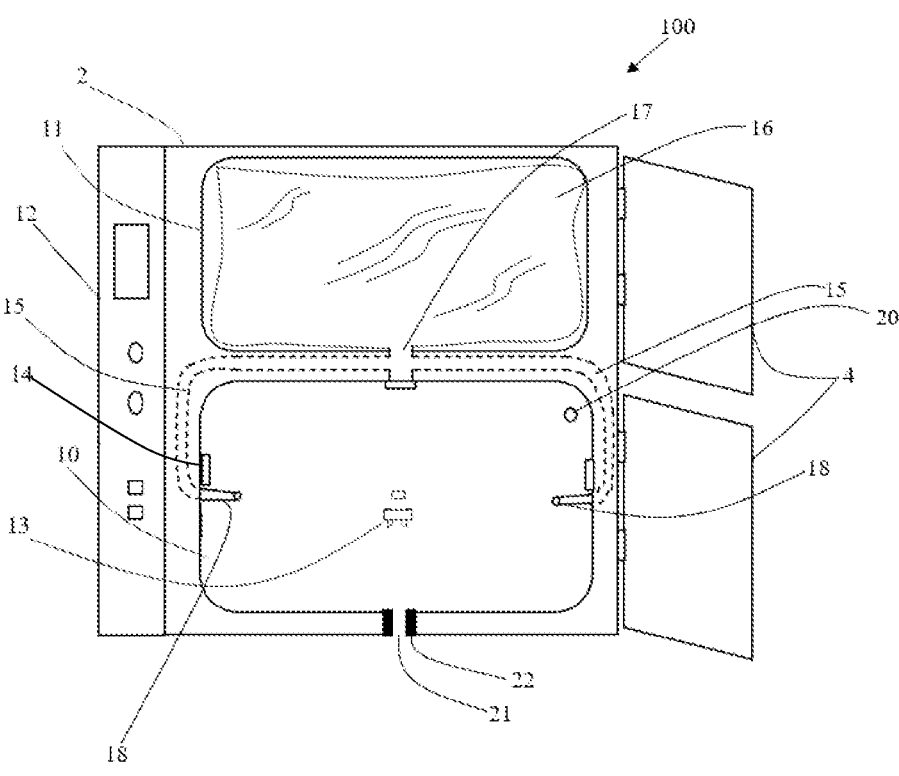
FIG. 1 is a front side schematic view of the automated device 100 for disinfection of stethoscope headpiece using dual means working simultaneously, according to an embodiment herein.
Figure 2:
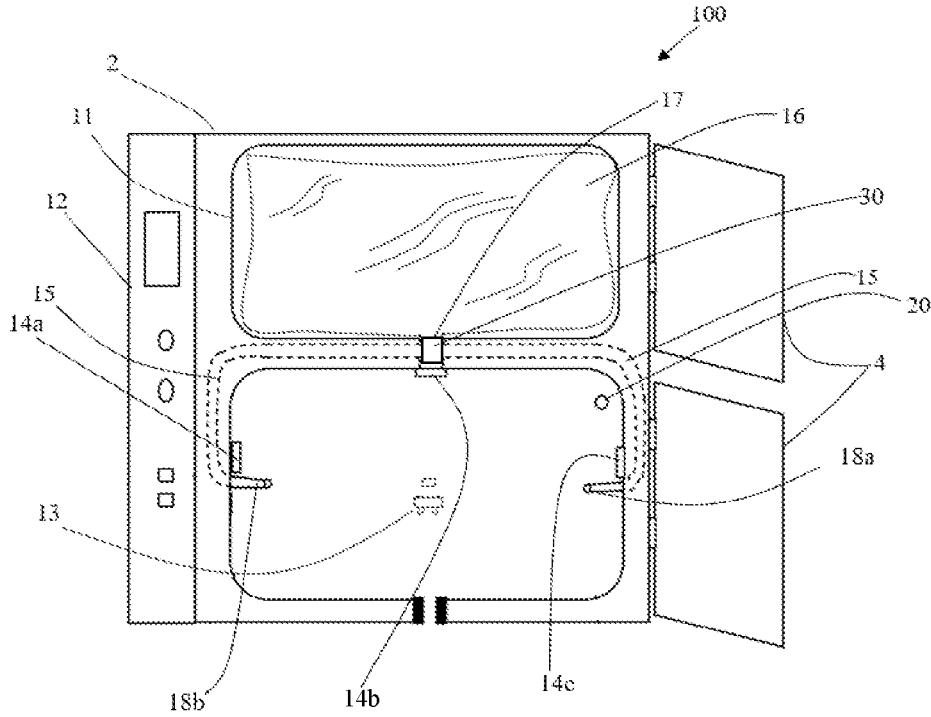
FIG. 2 is a front side schematic view of the automated device 100 for disinfection of stethoscope showing the UV-C light sources 14a to 14c, according to an embodiment herein.
Figure 3:
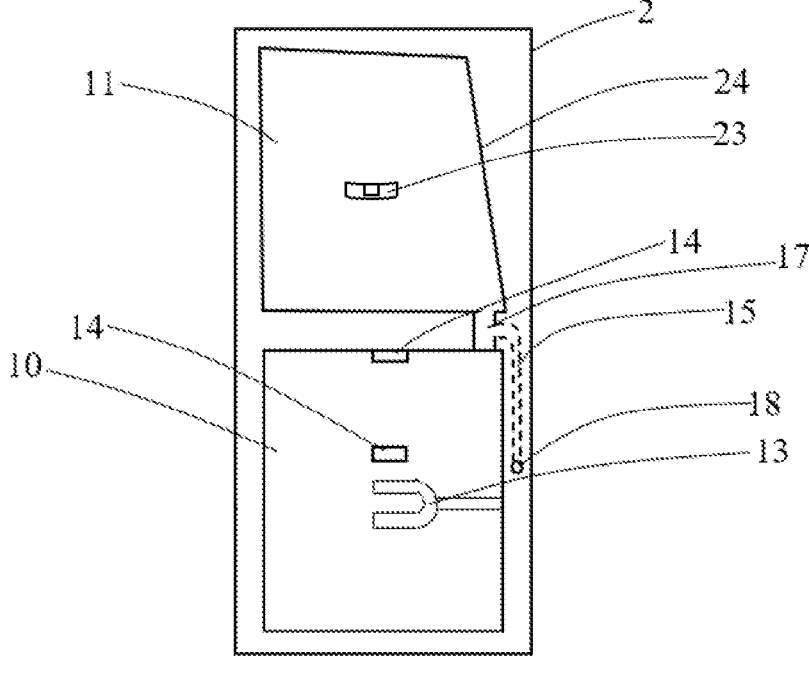
FIG. 3 is a right-side schematic view of the automated device 100 for disinfection of stethoscope headpiece using dual means working simultaneously, according to an embodiment herein.
Figure 4:
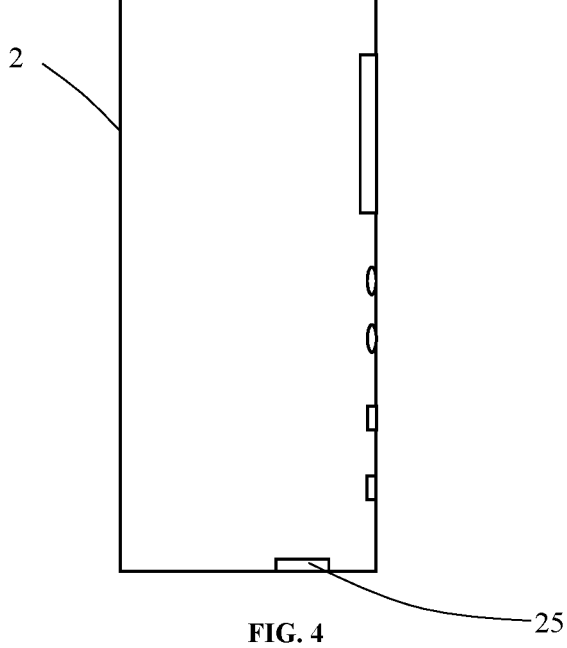
FIG. 4 is a left side schematic view of the automated device 100 for disinfection of stethoscope headpiece using dual means working simultaneously, according to an embodiment herein.

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical, electronic and other changes may be made without departing from the scope of the embodiments. The following detailed description is therefore not to be taken in a limiting sense.

The various embodiments herein provide an automated device for disinfection of stethoscope using dual means working simultaneously, especially the headpiece of stethoscope. The present invention provides a dual mode disinfection of the stethoscope headpiece using ultraviolet-C radiation and chemical means using a liquid for disinfection, wherein both the means are used simultaneously.

According to an embodiment herein, an automated device for disinfection of stethoscope comprises at least two chambers wherein a first chamber is a disinfection chamber, and a second chamber is a chemical holding chamber. The disinfection chamber comprises ultraviolet-C light sources which are present in an interior side of the chamber. The ultraviolet C light disinfects the stethoscope by breaking down chemical bonds of DNA, RNA and proteins of bacteria and viruses. While the chemical holding chamber acts a source of a liquid sanitizer which provide means for disinfection in the form of liquid spray.

With respect to FIG. 1 to FIG. 6*b*, an automated device 100 for disinfection of stethoscope headpiece using dual means working simultaneously is provided. The device 100 comprises a housing 2, at least two chamber present inside the housing 2, wherein one chamber is a disinfection chamber 10 and another chamber is a chemical holding chamber 11. The device 100 further comprises a plurality of spray tubes 15 and nozzles 18, a plurality of UV-C light source 14 present inside the disinfection chamber 10, a holder 13 present inside the disinfection chamber 10, at least two doors 4 hinged with the chambers 10 and 11, respectively, an air vent 20 present in the disinfection chamber 10, a bottom outlet 21 sealed with a rubber gasket 22 present at the bottom of the housing passing through the disinfection chamber 10 and a power supply.

According to an embodiment herein, the plurality of spray tubes 15 and nozzles 18 are present in the disinfection chamber 10.

According to an embodiment herein, the chemical holding chamber 11 is present on top side of the disinfection chamber 10.

According to an embodiment herein, the chemical holding chamber 11 holds a bag 16 of a chemical. The chemical is selected from the group consisting of alcohol or iso-propyl alcohol.

According to an embodiment herein, the holding chamber 11 has a slight slope 24 with top part of the chamber at higher elevation than the bottom part of the chamber. This allows the flow of the liquid to the outlet in vertical as well as horizontal position.

According to an embodiment herein, the plurality of spray tubes 15 deliver the chemical from the bag 16 kept inside the chemical holding chamber 11 to the disinfection chamber 10 through spray tubes 15 and nozzles 18.

According to an embodiment herein, the chemical moves out from an opening 17 present in the bag 16 to the spray tubes 15.

According to an embodiment herein, the holder 13 is a U-shaped holder which is detachable to hold a stethoscope head piece, and wherein the holder 13 is positioned at the centre of the disinfection chamber 10.

According to an embodiment herein, the nozzles 18 are communicated to the holding chamber 11 through a plurality of tubes 15.

According to an embodiment herein, the disinfection chamber 10 is equipped with the at least three ultraviolet-C ray disinfection lamps, wherein one is located on right, one on left and one on top side of the chamber 10.

According to an embodiment herein, the spray nozzles (18*a*, 18*b*) are located on a left side and a right side inner wall of the disinfection chamber 10.

According to an embodiment herein, the spray nozzles (18*a*, 18*b*) spray the chemical from the bag 16 on the stethoscope headpiece placed on the holder 13 inside the disinfection chamber 10 when a power button is 'ON'.

According to an embodiment herein, the bottom outlet 21 sealed with a rubber gasket 22 allows passage of the stethoscope tube.

According to an embodiment herein, the air vent 20 is located on at least one side of the disinfection chamber 10. The air vent 20 provides a ventilation to the disinfection chamber 10 when heated up and to allow escape of alcohol/ chemical vapours.

According to an embodiment herein, the chemical bag 16 is disposable and is replaced when the chemical gets over by opening the door. The bag 16 has a shape with slope on the back that will confine to the shape of the chamber. The outlet will be on the bottom side towards the back end (see FIGS. 7*a* to 7*d*).

According to an embodiment herein, a control panel 12 is present on the housing 2, wherein the control panel 12 comprises a plurality of control keys, a timer display, indicator lights, a controller and a power supply unit.

According to an embodiment herein, an external holder 23 is present on an outer side of the housing 2 for holding earpiece of the stethoscope.

According to an embodiment herein, the controller is equipped with a programmable microchip or microcontroller.

According to an embodiment herein, the stethoscope head piece disinfection device can be used in both vertical and horizontal orientation due to the slope on upper chamber.

According to an embodiment herein, the device 100 for disinfection of stethoscope headpiece using dual means working simultaneously includes a disinfection chamber 10 equipped with a disinfection means, a holding chamber 11 and a power supply with controller. The disinfection chamber 10 further comprises a hinged door 4, a U-shaped detachable stethoscope head piece holder 13, a pair of alcohol spray nozzles 18, and a plurality of ultraviolet-C ray disinfection lamps 14*a* to 14*c*, air vent 20; and a bottom outlet 21 sealed with rubber gasket 22. The holding chamber 11 further comprises a front hinged door 4, a disposable alcohol bag 16, and an alcohol bag outlet 17 with an attachment. The outer surface on the left side of the disinfection chamber 10 and the holding chamber 11 is provided with a plurality of control keys, a timing display, an indicator light, a charging unit, a controller and a power supply.

According to an embodiment herein, the disinfection means provided in the disinfection chamber 10 includes both UV-C radiation and chemical disinfection of stethoscope headpiece. $The disinfecting chamber 10 could also utilise any disinfection means which achieves the desired effect of disinfecting a stethoscope headpiece within a relatively short period of time.

According to an embodiment herein, the chemical disinfection of the stethoscope headpiece is done by using a pair of the alcohol spray nozzles 18 which sprays alcohol/chemical into the disinfection chamber 10.

According to an embodiment herein, the photo-disinfection is done by using ultraviolet-C ray disinfection lamps. The disinfection chamber 10 is equipped with the at least three ultraviolet-C ray disinfection lamps (14*a* to 14*c*), wherein one is located on right, one on left and one on top side of the chamber 10.

According to an embodiment herein, the disinfection chamber 10 is accessed through the front opening hinged door 4 providing easy access to the stethoscope support either for loading or unloading of the stethoscope.

According to an embodiment herein, the U-shaped detachable stethoscope head piece holder 13 is positioned at the centre of the disinfection chamber 10.

According to an embodiment herein, the shape of the stethoscope head piece holder 13 is similar to a "tuning fork". The stethoscope tube is secured inside the "U" of the "tuning fork". The U-shaped stethoscope head piece holder (13) is detachable to hold the stethoscope head piece of varying dimensions.

According to an embodiment herein, the alcohol spray nozzles 18 are located on the left and right sides inner wall of the disinfection chamber 10. $The alcohol spray originates from an alcohol source located in the holding chamber 11.

According to an embodiment herein, the pair of alcohol spray nozzles 18 are communicated to the holding chamber 11 through a pair of delivery tubes 15.

According to an embodiment herein, such use of ultraviolet-C light in the disinfection chamber 10 results in heating inside the chamber and alcohol disinfection creates alcohol vapor for which reason the chamber 10 is provided with an air vent 21 on at least one side of the chamber.

According to an embodiment herein, the air vent 21 is preferably located on the right side of the disinfection chamber 10.

According to an embodiment herein, the disinfection chamber further comprises outlet sealed with rubber gasket 22 at the bottom of the disinfection chamber 10 for passage of stethoscope tube. The gasket 22 also works as a seal for the outlet 21.

According to an embodiment herein, the holding chamber 11 further comprises: a front hinged door 4, a disposable chemical bag 16, and a bag outlet 17 with an attachment. The attachment acts as a fixation means for the bag to the outlet 17. The bag is disposable and is replaced after the liquid is over.

According to an embodiment herein, the holding chamber 11 has a slight slope 24 with top part of the chamber at higher elevation than the bottom part of the chamber for ease of flow of liquid from the disposable bag 16 in vertical as well as horizontal position. The holder 23 for holding stethoscope earpiece is located externally in the centre of holding chamber 11 externally on the housing 2. The holder 23 for holding stethoscope earpiece is curved "U" shaped for holding both the ear piece of stethoscope.

According to an embodiment herein, the holding chamber 11 is positioned at the top of the disinfection chamber 10, when the device is placed vertically.

According to an embodiment herein, the holding chamber 11 keeps and holds disposable chemical bag 16 in a vertical position such that the liquid easily passes through the outlet 17 into the tubes 15.

According to an embodiment herein, the hinged door 4 of the holding chamber 11 opens in front direction providing easy access for loading or unloading of the disposable alcohol bags.

According to an embodiment herein, the attachment 30 in the holding chamber 11 has two parts: a top part and a bottom part. According to an embodiment herein, the top part of the attachment connects with the alcohol bag 16 and the bottom part of the attachment connects with the pair of delivery tubes 15. These delivery tubes 15 enter from the left and the right sides of the disinfection chamber 10 and connects with the pair of spray nozzles 18.

According to an embodiment herein, the outer surface on the left side of the disinfection chamber 10 and holding chamber 11 is provided with a plurality of control keys, a timing display, an indicator light, a controller and a power supply.

According to an embodiment herein, the plurality of control keys, the timing display, the indicator light, the ultraviolet-C disinfection lamps, sprayer, and the power supply are all electrically connected with the controller.

According to an embodiment herein, the power supply to the device is chargeable.

According to an embodiment herein, the controller is equipped with a programmable microchip or microcontroller. The duration and intensity of the disinfection cycle is regulated by a programmable microchip or microcontroller.

According to an embodiment herein, the stethoscope head piece disinfection device can be used in both vertical orientation and horizontal orientation.

According to an embodiment herein, the precise means whereby the disinfection is affected may vary however it is envisaged that the provision of a unit capable of swiftly and efficiently disinfecting stethoscopes would diminish any possibility of cross contamination between patients and at the very least would protect a medical practitioner from exposure to a contaminated stethoscope through the head piece.

According to an embodiment herein, the head holder 13 is a detachable part which is like a tuning fork. The head holder 13 holds the stethoscope tube near the head piece within its prongs. The earpiece holder 23 is like a "C or U shaped" hanger on the side of the unit on which the earpiece will hang.

According to an embodiment herein, the working principle of the device of present invention is provided by first attaching a filled disposable alcohol bag 16 in holding chamber 11. Then, the hinged door 4 of the disinfection chamber 10 is opened and a stethoscope head piece is placed on the U-shaped detachable stethoscope head piece holder 13. The stethoscope tube is passed through the bottom outlet 21 sealed with rubber gasket 22. The hinged door 4 of the disinfection chamber 10 is closed. After closing the hinged door of the disinfection chamber, the control keys are pressed to a disinfection mode (spraying or ultraviolet, or can be combined with application), and a "disinfect" button is pressed to start the cycle. The indicator light will be 'ON' immediately on the start of disinfection process. The timer display shows the time elapsed from the start of cycle. During the process, the device of the present invention starts liquid spray disinfection through spray nozzles 18 simultaneously with the photo-disinfection of stethoscope head piece with the ultraviolet-C disinfection lamps 14 being ON.

Once the cycle is complete, the indicator light and ultraviolet-C disinfection lamps 14 will be "OFF".

According to an embodiment herein, the cycle terminates and ultraviolet-C disinfection lamps 14 gets "OFF" in case the hinged door 4 of the disinfection chamber 10 is opened when during a cycle. This is to protect eyes of user from exposure to ultraviolet-C light.

According to an embodiment herein, the device is equipped with a charging port 25. In case of low battery, an indicator light indicates low battery mode.

According to an embodiment herein, the device will show "alert" when the chemical bag is empty.

The controller or control unit in the device of present invention allows performing all operations completely automatically, since the duration and intensity of the disinfection cycle is regulated by a programmable microchip or microcontroller, providing, at the same time, safety for both the operator and the patient because the operation of the UV-C LED is inhibited if the device is not properly closed on stethoscope or opened before the completion of disinfection.

Figure 7A:
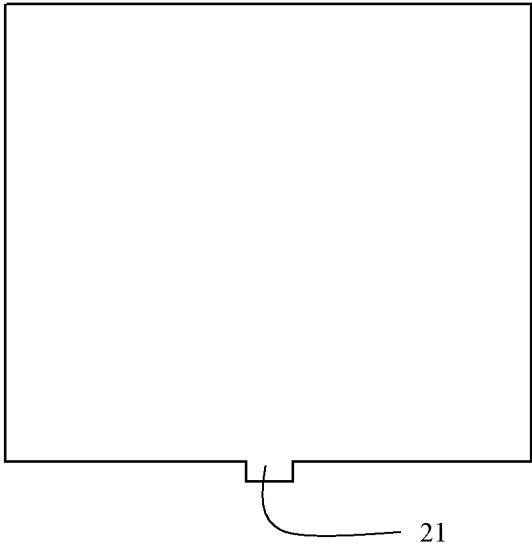
Figure 7B:
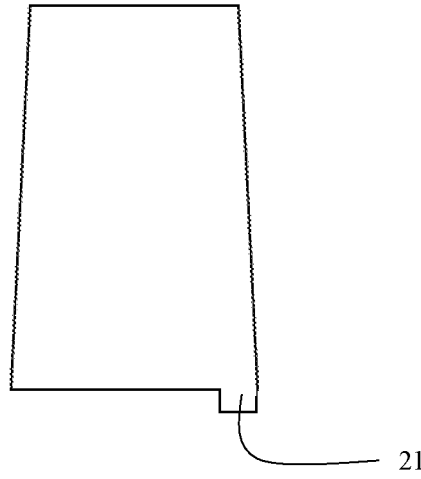
Figure 7C:
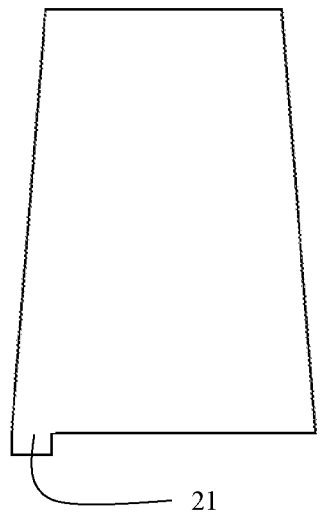
Figure 7D:
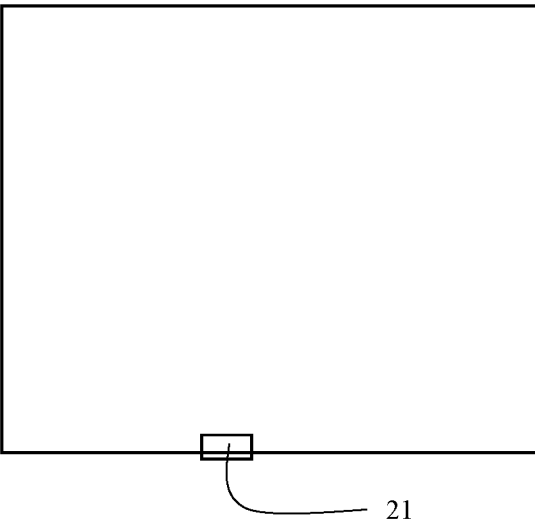

FIG. 7a to FIG. 7d shows the shape of the chemical bag 16, wherein FIG. 7a is a front view of the chemical bag, wherein FIG. 7b is a right-side view of the chemical bag, wherein FIG. 7c is a left side view of the chemical bag and wherein FIG. 7d is a back view of the chemical bag, according to embodiments herein. With respect to FIG. 7, the shape of the bag 16 is such that it fits the shape of the chemical holding chamber 11. This is a specially designed bag as per present invention. The bag has a sloppy edge and an outlet 21 for releasing the liquid in the disinfection chamber.

According to an embodiment herein, the device takes less than 3 minutes simultaneous disinfection of stethoscope headpiece.

The embodiments herein provide an automated device for disinfection of the stethoscope head piece. The disinfection means provided in the disinfection chamber of the device of present invention includes both photo-disinfection and chemical disinfection of stethoscope headpiece providing a dual effect. The device of the present invention is simple, efficient, and economical to make. The device is of minimal weight and is portable. The device of the present invention is compact in size as only the stethoscope head piece is deposited in the disinfection chamber and remaining part of stethoscope lies outside the disinfection chamber. The use of the ultraviolet-C LED disinfection lamps as photo-disinfection source allows the miniaturisation of the device of present invention.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the claims presented in the complete specification or non-provisional application.

I claim:

1. An automated device (100) for disinfection of stethoscope headpiece using dual means working simultaneously, comprises:
    a housing (2);
    at least two chamber present inside the housing (2), wherein one chamber is a disinfection chamber (10) and another chamber is a chemical holding chamber (11);

a plurality of spray tubes (15) and nozzles (18), wherein the plurality of spray tubes (15) and nozzles (18) are present in the disinfection chamber (10);
    a plurality of UV light source (14) present inside the disinfection chamber (10);
    a holder (13) present inside the disinfection chamber (10);
    at least two doors (4) hinged with the chambers (10) and (11), respectively;
    an air vent (20) present in the disinfection chamber (10);
    a bottom outlet (21) sealed with a rubber gasket (22) present at the bottom of the housing passing through the disinfection chamber (10); and
    a power supply.

2. The device as claimed in claim 1, wherein the chemical holding chamber (11) is present on top side of the disinfection chamber in vertical orientation (10).

3. The device as claimed in claim 1, wherein the chemical holding chamber (11) holds a bag (16) of a disinfection chemical.

4. The device as claimed in claim 3, wherein the chemical moves out from an opening (17) present in the bag (16) to the spray tubes (15).

5. The device as claimed in claim 3, wherein the bag (16) is disposable and is replaced when the chemical gets over by opening the door.

6. The device as claimed in claim 3, wherein the bag (16) is shaped in a way to fit the shape of the chemical holding chamber (11).

7. The device as claimed in claim 1, wherein the holding chamber (11) has a slight slope (24) with top part of the chamber at higher elevation than the bottom part of the chamber allowing the flow of disinfection chemical to the outlet in vertical as well as horizontal position.

8. The device as claimed in claim 1, wherein the plurality of spray tubes (15) deliver the chemical from the bag (16) kept inside the chemical holding chamber (11) to the disinfection chamber (10) through spray tubes (15) and nozzles (18).

9. The device as claimed in claim 1, wherein the holder (13) is a U-shaped holder which is detachable to hold a stethoscope head piece, and wherein the holder (13) is positioned at the centre of the disinfection chamber (10).

10. The device as claimed in claim 1, wherein the nozzles (18) are communicated to the holding chamber (11) through a plurality of tubes (15).

11. The device as claimed in claim 1, wherein the disinfection chamber (10) is equipped with the at least three ultraviolet-Cray disinfection lamps, wherein at least one lamp (14a) is present on a left side of the disinfection chamber (10), wherein at least one lamp 14b is present on a top side of the disinfection chamber (10, and wherein at least one lamp (14c) is present on a right side of the disinfection chamber (10).

12. The device as claimed in claim 1, wherein the spray nozzles (18a, 18b) are located on a left side and a right side inner wall of the disinfection chamber (10).

13. The device as claimed in claim 1, wherein the spray nozzles (18a, 18b) spray the chemical from the bag (16) on the stethoscope headpiece placed on the holder (13) inside the disinfection chamber (10) when a power button is ON.

14. The device as claimed in claim 1, wherein the bottom outlet (21) sealed with a rubber gasket (22) allows passage of the stethoscope tube.

15. The device as claimed in claim 1, wherein the air vent (20) is located on at least one side of the disinfection chamber (10).

16. The device as claimed in claim 1, wherein a control panel (12) is present on the housing (2), wherein the control panel (12) comprises a plurality of control keys, a timer display, indicator lights, a controller and a power supply unit.

17. The device as claimed in claim 16, wherein the controller is equipped with a programmable microchip or microcontroller.

18. The device as claimed in claim 1, wherein an external holder (23) is present on an outer side of the housing (2) for holding an earpiece of the stethoscope.

19. The device as claimed in claim 1, wherein the stethoscope head piece disinfection device can be used in both vertical and horizontal orientation.

20. The device as claimed in claim 1, wherein the device takes less than 3 minutes for disinfection of stethoscope headpiece using photo-disinfection and chemical disinfection methods simultaneously.

\* \* \* \* \*